United States Patent [19]
Marlow et al.

[11] Patent Number: 6,001,308
[45] Date of Patent: Dec. 14, 1999

[54] DETONATION/DEFLAGRATION PRECURSOR DETECTION OF GASES, VAPORS, AEROSOLS, AND MIXTURES THEREOF

[75] Inventors: William H. Marlow; John P. Wagner, both of College Station, Tex.

[73] Assignee: MW Technologies, Incorporated, College Station, Tex.

[21] Appl. No.: 09/023,313

[22] Filed: Feb. 13, 1998

Related U.S. Application Data

[63] Continuation of application No. 08/539,504, Oct. 6, 1995, Pat. No. 5,789,256, which is a continuation of application No. 08/227,618, Apr. 14, 1994, abandoned.

[51] Int. Cl.$^6$ .................................................. G01N 25/54
[52] U.S. Cl. ............................. 422/94; 422/78; 422/90; 422/91; 436/155; 436/156
[58] Field of Search ........................... 422/58, 78, 90–91, 422/94; 436/155, 156, 159

[56] References Cited

U.S. PATENT DOCUMENTS

| | | |
|---|---|---|
| 3,844,716 | 10/1974 | Noakes . |
| 3,997,416 | 12/1976 | Confer . |
| 4,019,863 | 4/1977 | Jenkins et al. . |
| 4,201,550 | 5/1980 | Noszticzius et al. . |
| 4,348,888 | 9/1982 | Snee . |
| 4,469,574 | 9/1984 | Keehn et al. . |
| 4,532,219 | 7/1985 | Hagen et al. . |
| 4,666,678 | 5/1987 | Lemelson . |
| 4,702,808 | 10/1987 | Lemelson . |
| 4,927,766 | 5/1990 | Auerbach et al. . |
| 5,070,024 | 12/1991 | Bruno . |
| 5,789,256 | 8/1998 | Marlow et al. .................. 436/156 |

OTHER PUBLICATIONS

W. C. Gardiner et al, *J. Chem. Phys.* 1966, 44, 4653–4654.
P. Gray et al, Symp. (Int.) Combust., [Proc.] 1967, 11, 1123–1131.
D. S. Burgess et al, U.S. Bureau of Mines Report #7196.
A. R. Ubbelohde et al, Symp. (Int.) Combust., [Proc.] 1969, 12, 809–818.
D. F. Cook et al, Symp. (Int.) Combust., [Proc.] 1971, 13, 757–766.
R. I. Soloukhin *Astronaut. Acta.* 1972, 17, 633–638.
M. E. Nolan *Combust. Sci. Technol.* 1973, 7, 57–63.
J. W. Meyer et al, *Combust. Sci. Technol.* 1973, 8, 185–197.
S. Crescitelli et al, *Riv. Combust.* 1974, 28, 210–220.
P. D. Ronney et al, *Combust. Flame* 1985, 62, 121–133.
M. Esseghir et al, *Combust. Flame* 1988, 73, 99–105.
S. Fukutani et al, *Nenryo Kyokaishi* 1990, 69, 946–951.
A. V. Chaschinou et al, *Ugol' Ukr.* 1992, 41–44.
H. Oestmark et al, *J. Anal. Appl. Pyrolysis* 1992, 24, 163–178.

(List continued on next page.)

*Primary Examiner*—Arlen Soderquist
*Attorney, Agent, or Firm*—Rosenthal & Osha L.L.P.

[57] ABSTRACT

The present invention and its claims encompass principles, methods, apparatus, and applications for detection, quantification, and monitoring of responses of gases, vapors, aerosols, and mixtures thereof to initiators of exothermic reactions. While the invention can be utilized for any concentration level, the intended, normal utilization is for gases in which the concentrations of species capable of participating in exothermic chemistry are too low to support self-sustaining exothermic reactions leading to detonations or deflagrations as well as for gases in which other factors prevent the exothermic reaction chemistry from becoming self-sustaining. This abstract shall not be construed to define or limit in any way the scope of the invention, which is measured by the appended claims.

15 Claims, 3 Drawing Sheets

OTHER PUBLICATIONS

M. G. Kim et al, *Proc. SPIE–Int. Soc. Opt. Eng.* 1993, 1801, 392–399.
S. R. Jain Proc. Natl. Symp. Therm. Anal. 1993, 9, 12–16.
W. E. Maher et al, *J. Appl. Phys.* 1975, 46, 761–772.
R. G. Macdonald et al, *J. Chem. Phys.* 1977, 66, 3598–3608.
J. H. Kiefer et al, *Rev. Sci. Instrum.* 1981, 52, 1392–1396.
A. J. Tulis et al, *Rev. Sci. Instrum.* 1982, 53, 1586–1591.
M. G. Kim et al, *Chem. Asbtr.* 1993, 119, 190919c.
Fluckiger, D., H.D. Lin, and W. H. Marlow. 1985. Composition Measurement Of Aerosols Of Submicrometer Particles By Phase Fluctuation Absorption Spectroscopy. *Applied Optics* 24 No. 11, 1668–1681.
Wagner, J. P., 1977. Smoke Detector Characteristics. Second International Conference On Fire and Safety University of San Francisco.

Wagner, J. P. and Fookson, A., 1977. Application Of Fire/Gas Sensor Detection Technology To Metal And Non–Metal Mine Fire Problems. Fire Research Abstracts and Reviews, National Academy Of Sciences–National Research Council, Washington, D.C.

Wagner, J. P., Fookson, A., and May, M.; 1976; Performance Characteristics Of Semiconductor Sensors Under Pyrolytic, Flaming, and Smoldering Combustion Conditions. J. Fire and Flammability, 7, 71–103.

D. W. Singleton *J. Oil Colour Chem. Assoc.* 1976, 59, 363–368.

ns of U.S. application Ser. No.
DETONATION/DEFLAGRATION PRECURSOR DETECTION OF GASES, VAPORS, AEROSOLS, AND MIXTURES THEREOF This is a continuation of U.S. application Ser. No. 08/539,504, filed Oct. 6, 1995, which is a continuation of U.S. application Ser. No. 08/227,618, filed Apr. 14, 1994 (abandoned).

REFERENCES CITED

Fluckiger, D., H. B. Lin, , and W. H. Marlow. 1985. Composition measurement of aerosols of submicrometer particles by phase fluctuation absorption spectroscopy. *Applied Optics* 24 No. 11, 1668–1681.

Wagner, J. P. 1977. Smoke detector characteristics. Second International Conference on Fire and Safety, University of San Francisco.

Wagner, J. P., and A. Fookson. 1977. Application of fire/gas sensor detection technology to metal and non-metal mine fire problems. *Fire Research Abstracts and Reviews, National Academy of Sciences-National Research Council*, Washington,D.C.

Wagner, J. P., A. Fookson, and M. May. 1976. Performance characteristics of semiconductor sensors under pyrolytic, flaming and smoldering combustion conditions. J. *Fire and Flammability*, 7, 71–103,

BACKGROUND OF THE INVENTION

The present invention relates to a new principle for the detection, quantification, and monitoring of gas-borne materials capable of exothermic reactions. The methods, apparatus, and applications following from this principle and encompassed by this patent are intended for applications to gases, vapors, aerosols, and mixtures thereof.

Throughout numerous industries and in diverse workplaces, hazards arise from detonations and/or deflagrations involving gas-borne materials. The hazards occur when exothermic chemical reactions (i.e. combustion) of these materials are initiated under conditions which permit the reaction chemistry to become self-sustaining thereby allowing it to propagate through the gas. In the case of detonations, both heat and a large pressure rise accompany the propagation of a shock wave. For deflagrations, the propagation is associated principally with temperature rise and a pressure rise for rapidly moving deflagrations.

In practical settings, ignition sources for the exothermic chemistry can be due to electrostatic discharge (e.g., arcs, sparks from motors, static discharge due to accumulated charge), glowing or open flame (e.g. cigarette, welding torch), hot surfaces, or even spontaneous combustion. Examples of accidents include grain elevator damage or total destruction due to dust explosion, plastics manufacturing, shaping, or other processing facility explosions, coal mine explosion, petrochemical processing plant explosion or fire, gas storage or transfer location explosions, and innumerable less spectacular accidents in which the extent of deaths and injuries and damage to structures, materials, and equipment are more limited.

To avoid accidental detonation or deflagration, a number of different steps are available, depending upon the particular circumstance. Where feasible, measures are taken to prevent hazardous concentrations of combustible materials from accumulating in the local atmosphere. Whenever this is unreliable or impractical, as in the transport and handling of fine particulate materials, at chemical processing, transfer, and storage locations, in hazardous waste sites, and elsewhere, warning sensors and detonation/deflagration suppressers are commonly utilized. In all cases, extensive measures to avoid any ignition sources are generally taken. For some circumstances such as welding of tanks previously containing combustible liquids and industrial processes, hazardous conditions are always possible and there is little that can be done other than conduct the processes or activities in a prudent manner even if the hazard itself is poorly quantified.

Common to almost all detonation/deflagration hazard avoidance measures are the needs for sensors to indicate the status of the potential for hazard. When preventative measures are utilized, methods to determine the effectiveness of those measures are required. Regardless of whether sensing the potential for detonation and deflagration is the primary measure, the secondary measure, or utilized in ventilation or process control, the detectors must be effective, reliable, accurately indicate the actual hazard, and require a minimum of maintenance.

PRIOR ART

For hazards due strictly to gases, at least the following classes of sensor methodologies are currently utilized: (1) quantification of the concentration or determination otherwise of the presence of either single gas species, multiple specific gas species, or classes of gases by use of specific gas detectors. Examples include gas chromatographs, photoionization sensing, mass spectrometry, electrochemical sensing, infrared gas analyzers, polymeric film sensors, and Drager tubes; (2) detection of changes in thermal conductivity of the gas; (3) monitoring of chemical products of combustion such as $CO_2$; (4) catalytic oxidation sensors; (5) semiconductor sensors such as the Taguchi sensor which changes its resistivity upon adsorption of oxidizable gases, vapors, and/or particles; and (6) ceramic sensors For hazards due to "dusty gas" or aerosol, the warning methods monitor either total optical turbidity (light attenuation) or size distribution as given by multi-wavelength turbidity measures. Variants on this approach include both sampled and remote monitoring methods indicating either light attenuation or back-scattering from the airborne particles. In other words, these methods measure the interaction of a beam of light with particles (or dusts or aerosols) in the gas. A second approach that may be cited is the various "smoke" detectors that sense the particulate products of combustion through their effects on the electrical conductivity of the air containing the smoke (ionization detectors) or again through light scattering methods (as above) or refraction methods (see Wagner and Fookson, 1977).

For hazard arising from the synergistic combination of gas and aerosol, no sensor currently exists other than can be constructed by the combination of the methods cited in the two preceding paragraphs.

Deficiencies of Prior Art—Gas Detectors (1) Composition, or species, detection is useful when the gases which cause the hazard are completely known in advance. This approach has questionable merit when the potential for complete, prior identification of the hazardous gases is limited and when mixtures of gases that individually constitute no hazard but which together could pose a hazard are present. Furthermore, if an otherwise inert aerosol concentrates the combustible vapors on its surfaces via adsorption or condensation, no hazard will be identified and yet the chemical species may still be available to react either if they subsequently evaporate or if they can sustain combustion via reactions involving the aerosol surfaces.

(2) Thermal conductivity changes of the gas are an indicator of incipient combustion due to the temperature dependence of conductivity in a gas. Since this approach senses combustion in its earliest stages, it does not provide an advance warning and is thus not directly comparable with what is claimed in this invention.

(3) Monitoring of the chemical products of combustion is entirely comparable with thermal conductivity in the sense that they both detect combustion that has already started.

(4) Catalytic oxidation sensors directly measure the presence of molecular species which undergo combustion. Unlike specific species sensors, they include all molecular species that are present. However, they cannot detect hazards related to the presence of aerosol as discussed in (1) above. Furthermore, these sensors are especially prone to surface poisoning and/or fouling from various chemicals found in the work place such that their readings become unreliable.

5) While the Taguchi sensor responds to oxidizable or combustible gases and vapors as well as incomplete products of combustion (e.g., CO, NO) the need for a flame arrestor (typically 100 mesh screen) to prevent ignition in combustible atmospheres from its heated sensing element precludes its use in dusty atmospheres. That is, dusts plug or clog the fine openings of the flame arrestor. Particles and semivolatiles which may or may not be combustible deposit upon and pyrolyze on the sensor surface thereby fouling it and reducing its sensitivity. Finally, there are interferences from other gases. See Wagner, 1977, and Wagner, Fookson, May, 1976.

6) In the absence of information on the mode of operation in company brochures, we infer that the ceramic sensors are similar to the Taguchi sensors and are therefore prone to similar operational problems.

Deficiencies of Prior Art—Aerosol Detectors

All methods utilizing light scattering or turbidity require prior knowledge of the aerosol and its detonation hazard as it depends upon both the mass of the aerosol and how the mass is distributed among the various sizes of particles that comprise the aerosol. This approach is adequate only under the most restrictive conditions because changes in the aerosol or the surrounding atmosphere which are not detected can substantially affect the detonation hazard. These include changes in the relative humidity, background gas species, sorbed or condensed molecular species on the aerosol surface, and mass distribution of the aerosol.

Generic Deficiencies of Prior Art

Common to all classes of existing sensors is the inability to quantify hazard from mixtures of aerosols and gases. While hazardous gases and aerosols may each be present in densities that by themselves present no hazard, taken together they can be extremely dangerous.

Poisoning is another practical difficulty that afflicts several of the most widely-used sensors. When the active sensing element of the sensors, such as the catalytic oxidation sensor and some species detectors, are exposed to realistic industrial environments, they frequently encounter gases or aerosols which deposit on their surfaces and render them inactive or provide un-interpretable responses. Experience indicates that for this reason, such sensors are often unreliable and alarm conditions are actually ignored in practice. Additionally, remote, or area, sensing systems that involve surfaces exposed to the atmosphere in question can find their usefulness degraded by the deposition of materials on those surfaces. Since such optical methods only passively probe the atmosphere, signal attenuation due to fouling of observed surfaces is indistinguishable from signal attenuation due to the materials which are intended to be detected.

OBJECTIVES OF THE INVENTION

The primary objective of this invention is the creation of a new principle for the detection, quantification, and monitoring of gas-borne materials including gases, vapors, aerosols, and mixtures thereof which are capable of exothermic reactions.

Another objective of this invention is the creation of methods for practical realization of this new principle.

Another objective of this invention in the creation of new classes of sensors of these gas-borne materials capable of participating in exothermic reactions and which sensors are based on these methods for practical realization of the new principle.

Another objective of this invention is the creation of safety and control devices as well as analytical instrumentation which follow from the utilization of these sensors and which devices and instrumentation are not subject to difficulties of principle and practice of prior art.

Another objective is to facilitate protection of personnel, materials, and equipment and for systems or process monitoring or control based upon detonation/deflagration nation/deflagratrion potential of the environment or gas system of interest as provided by these devices and instrumentation. Their functions will be to indicate need to take remedial actions or to terminate the processes, procedures, or practices which are contributing to the presence of materials in the gas phase that can lead to detonation or deflagration hazard if the concentrations of those materials increase subsequent to the time when the devices issue their warnings. Additionally, these devices could be employed when conditions may already be unsafe for practices that would initiate detonation or deflagration.

A still further objective is to create control devices in systems approaches to regulate ventilation airflows designed to maintain vapor, gas and/or dust level below minimum explosive limits or limits defined by other criteria that can be related to the quantity measured by these sensors such as permissible exposure limits (PEL) for exothermically reactive toxic vapors.

A still further objective of this invention is to facilitate applications of the principle, methods, and devices for applications that are either derivative of their detonation/deflagration hazard sensing capabilities or are of use for a wide spectrum of other analytical and industrial purposes.

SUMMARY OF THE INVENTION

This patent is for a new principle of detection and quantification whose purpose is to determine the exothermic response of gas-borne materials to an initiator of exothermic reactions and for devices that follow from the implementation of the principle.

The Minimum Explosive Concentration (MEC) for a gas-borne material (gas, vapor, and/or aerosol) is its concentration at which an initiator of combustion causes its detonation or deflagration due to the presence of the minimum density of that material required to propagate the reaction chemistry with no additional stimulus. At lower concentrations, detonation/deflagration cannot occur because the exothermic chemistry is not self-sustaining. In other words, the reactive species, heat and/or pressure released locally due to an initiator are dissipated or quenched by the background gas (e.g. air) without igniting exothermic reactions beyond the very localized region of the initiator. Nevertheless, the initiator does cause a transient response by the background gas which is dependent upon the presence and quantity of materials capable of exothermic reactions. The response of the background gas to concentrations of exothermically reactive materials below the MEC is what is here called a "precursor". Products (i.e., sensors, detectors, control devices, apparatus, gadgets, instruments, instrumentation, design and methodology, set-ups, either hand held, portable or fixed; line, solar, fuel or battery operated for commercial applications or otherwise) which detect and quantify the responses of the background gas to initiators of exothermic reaction chemistry either as precursors or as potential detonations or deflagrations using a variety of sensors based on monitoring changes in the gas by different physical principles (e.g., optical, thermal, pressure, sound, ion flux or electrical conductivity) are all the subjects of this patent. dr

BRIEF DESCRIPTION OF THE DRAWINGS

As indicated above, this invention is for a new principle of detection and measurement and for the devices that follow from it. Therefore, drawings of its implementation can only be illustrative, not inclusive. The drawings are given for the purpose of indicating the relative locations of components, their functions, and their interactions (see FIG. 1). In no way is the illustrative representation as given in FIG. 1 to be considered as limiting the scope, configuration, components, operation, data interpretation and utilization, or applications for this patent.

In FIG. 2 from one side, the length of the sample chamber is represented as a cylindrical tube. In FIG. 3, a representation of the sample chamber with a view perpendicular to the plane illustrated in FIG. 2 is given and it illustrates the path of a light beam passing through the sample during a measurement. Numerous details such as inlet and outlet valves and seals (located at 2 in the figures), system actuation, signal recording and processing, etc. are omitted.

DETAILED DESCRIPTION OF ILLUSTRATIVE EMBODIMENT OF THE INVENTION

Figure 1:
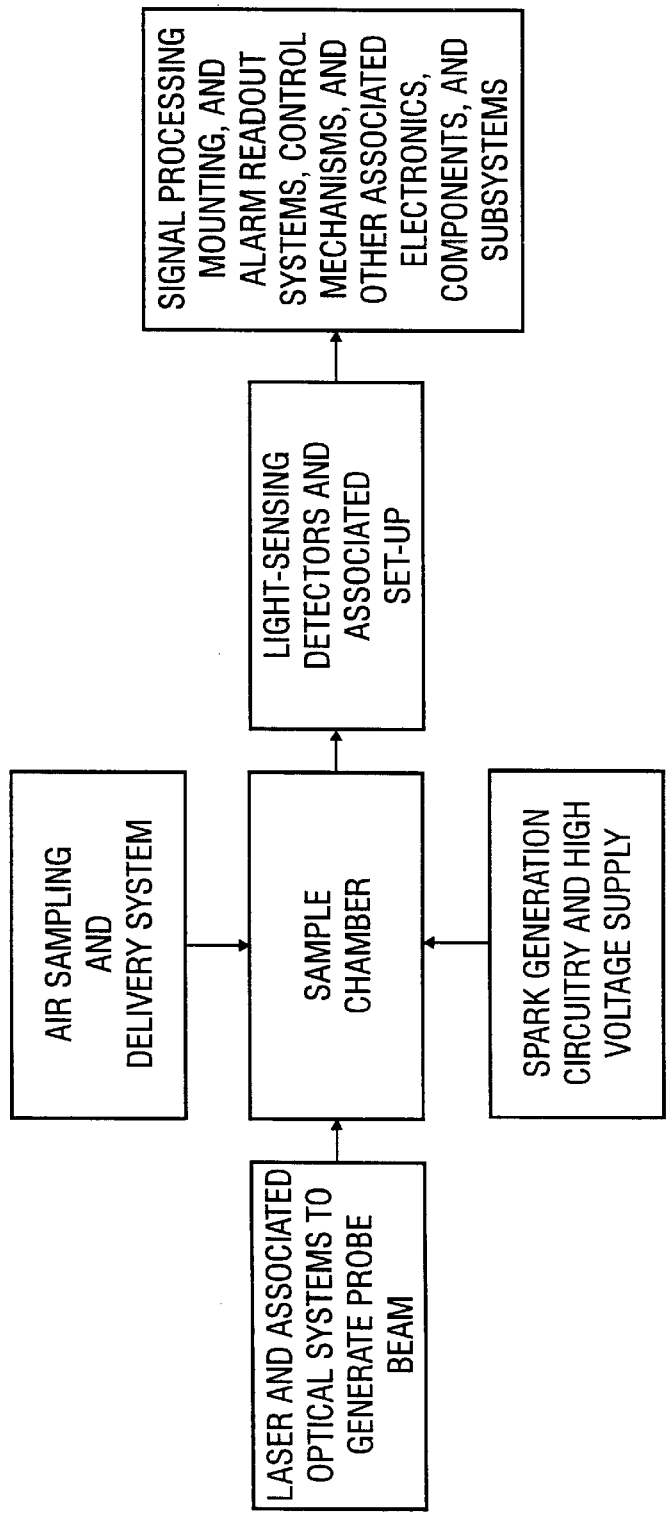
Figure 2:
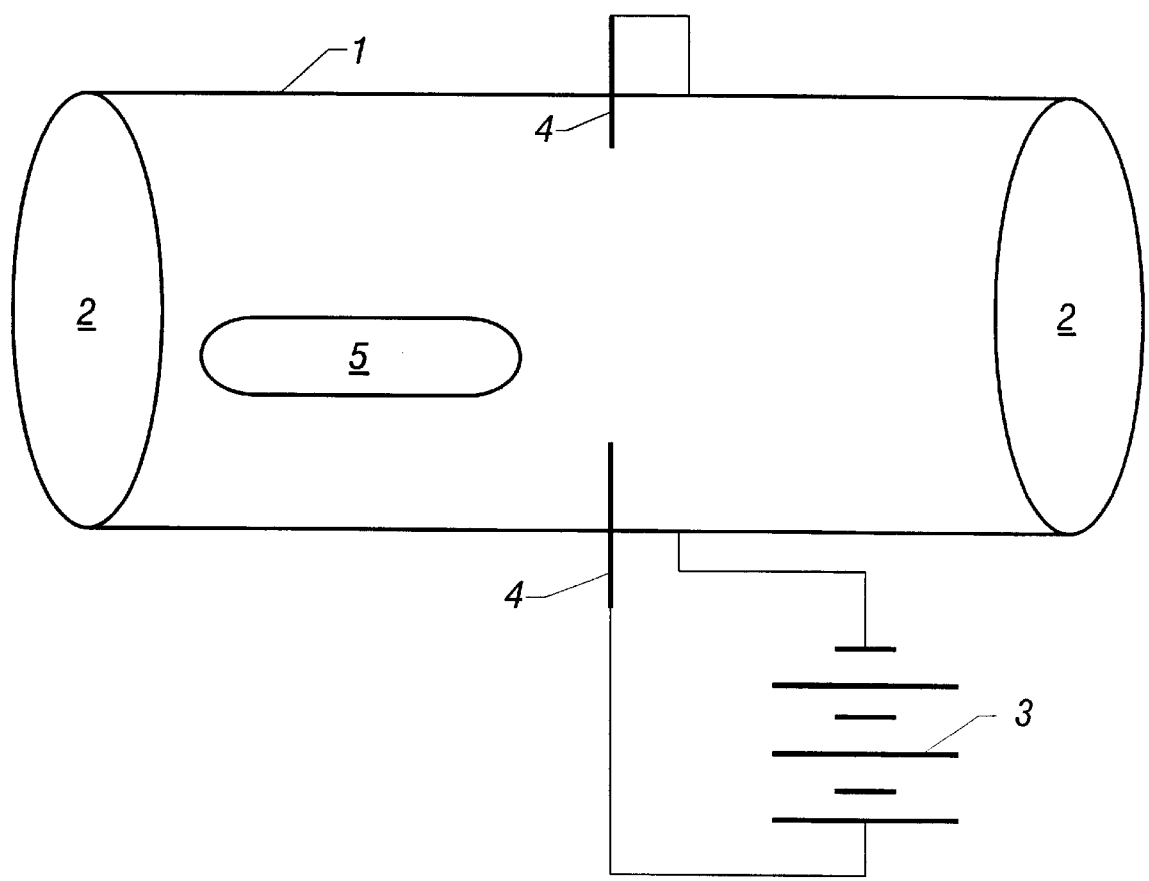
FIGS. 2 and 3 give two views of the principal elements of a sensing system that illustrate the basis of this invention.
Figure 3:
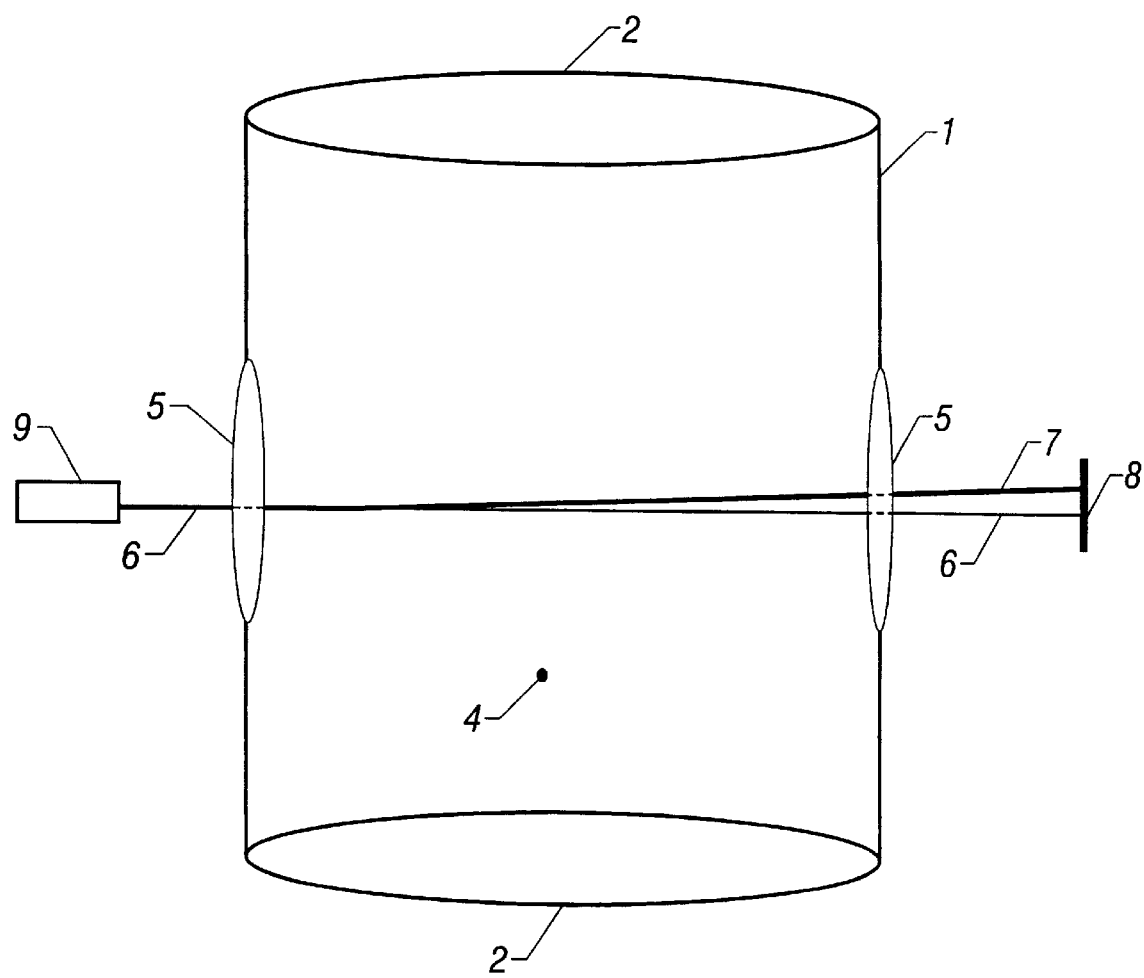

In this illustrative depiction of the invention, FIGS. 2 and 3 display the measurement chamber 1 consisting of a tube, which in practice may be oriented vertically for downward air flow. In FIG. 2, two electrodes 4 penetrate the tube 1 and are spaced such that voltage 3 supplied across them causes a single spark (the initiator) to jump with sufficient energy dissipation to ignite any anticipatible sample. In practice this requires a minimum of 0.2 millijoule for certain hydrocarbon gases and vapors under ideal combustion conditions and up to 1.0 joule of energy for dusts of relatively large particle sizes with the discharge in dry air requiring 15–30 kV for a spark gap in the 0.5 to 1.0 cm range. The position of the electrodes requires the spark to cross the chamber centerline, for convenience. Windows, 5, are located on opposing sides of the tube. As illustrated in FIG. 3, their function is to allow the light beam 6 from the (laser) light source 9 to pass through the tube 1 while the interior surface of the tube remains smooth and free of leaks. The windows may optionally be arranged to allow flows of sheath air free of particles and condensable vapors to pass over them while the sampled air flows through the tube. Alternatively, arrangements allowing for rotation and/or cleaning at designated intervals are entirely feasible. In FIG. 3 illustration is given of the position of the light beam, 6 or 7 as it leaves the tube 1. Its intensity, or a related quantity, is detected by the light-sensitive detector 8 which may be any of several different devices including position-sensitive detectors or photodiode sensors. Note that both the source 9 of the measuring signal (the laser) and the sensor 8 (e.g. photodiode or position-sensitive detector) for that signal are entirely external to the measurement apparatus. Therefore, they may be sealed from environmental degradation with only the easily monitored and cleaned windows subject to materials deposition from the sample stream.

In operation, air to be measured is drawn through the sample testing chamber 1 and subsequently the inlet and exhaust ports, 2, are closed or other measures taken to prevent ignition external to the chamber. A single spark due to the voltage source 3 is immediately discharged across the electrodes 4. In the measurement, the light beam 6 is briefly deflected or scattered from its unperturbed path due to the effects on the index of refraction of the transient heat and pressure rise of the test-chamber air through which the light beam passes. In FIG. 3, this deflection is illustrated by the alternative light path 7 that is not collinear with the unperturbed light 6. The temperature/pressure transient causing the perturbation in the light path can arise from two sources only: (1) the dissipation of only the energy deposited in the air by the spark; (2) energy released by exothermic reaction chemistry initiated by the spark. Various measurement strategies are available for distinguishing between these two signal sources. One is to interrogate the gas at a sufficiently large distance from the spark that no signal, i.e. perturbation of the light beam, in the absence of exothermic chemistry is measured. In this case, if a perturbation is measured at that location, then the sole cause of the measured perturbation of the light path is the temperature and pressure rise caused by the exothermic reaction chemistry. A second measurement strategy is to quantify the magnitude of the temperature/pressure transient by the amplitude, duration, and other characteristics of the perturbation of the laser beam relative to those same responses in the absence of exothermically reactive materials. A third is to measure such characteristics as time delay, amplitude, and duration of the transients at multiple positions located on one side of the spark or on both sides of the spark, again relative to those same responses in the absence of exothermically reactive materials. Note in all cases that the signal to be measured is generated in the gas and is thus not subject to degradation as is true for prior art sensors for which the signal is generated at a sensor surface due to reactions at that surface.

DETAILED DESCRIPTION OF THE INVENTION

To describe the principles of this invention, a brief explanation of the physical conditions involved in a detonation or deflagration is helpful: Exothermic chemical reactions of a trace-gas or aerosol result in local increases in temperature and/or pressure as well as reactive chemical species including ions, free radicals, and molecular fragments that propagate the reaction chemistry. If the background gas is incapable of dissipating or quenching these physical and chemical products of the exothermic chemistry as rapidly as the exothermic reaction chemistry produces them, then a detonation or deflagration can occur, providing other conditions are correct; conversely, if the gas does not sustain the reaction chemistry and dissipates the heat and/or pressure generated by the exothermic reactions more rapidly than it is generated, then no hazard exists regardless of other conditions.

Prior to the accumulation of reactants in sufficient densities to sustain a detonation or deflagration, graded responses to initiators for this reaction chemistry occur. Here, an initiator is defined to be a condition imposed on the gas which forces to completion all thermally-initiated (and possibly otherwise initiated) chemistry which is possible for the gas-borne species in a highly localized volume of the gas. In the vicinity of a spark discharge, the weak plasma which is created accomplishes this objective by heating the gas far above its lower temperature threshold for reaction and by formation of the highly reactive species alluded to above. Since an electrical discharge is a realistic cause for detonations and deflagrations in practice, it is appropriate also in the quantification of true potential hazard because it can initiate only those reactions which the gas under examination is capable of supporting with no additional assumptions such as are implicit in all other methods as discussed above in prior art. Other initiators may also be used such as a focused microwave or infrared beams as are possible with masers and infrared lasers, respectively. Alternatively, molecule-specific initiation in the future may be possible by excitation of specific reactive bonds which induce exothermic chemistry of a specific molecular species by stimulating it to a reactive state in which it could undergo exothermic chemical reactions with surrounding gas molecules, most notably oxygen. Finally, initiation may occur through autoinitiation which is defined as self-ignition of the gas such as may occur either spontaneously or in the presence of a suitable reaction catalyst. Two examples of autoinitiation are the following: (1) A local, transient hot spot develops due to exothermic chemistry among chemical species that enter the gas phase; (2) thermodynamic conditions (generally externally impressed) induce initiation of exothermic chemistry.

The response of the gas to an initiator is a localized temperature/pressure perturbation, fluctuation, or transient in which the gas temporarily sustains elevated temperatures and/or pressures by propagating a temperature/pressure pulse which decays beyond the initiator zone. The source of this perturbation is the energy released in the initiator zone (1) due to exothermic reaction chemistry and (2) due to the initiator-zone processes which are independent of any exothermic reaction chemistry other than ionic and molecular recombinations which return the gas to its chemical state prior to the spark discharge. Regardless of the particular details of how it is generated, any temperature/pressure response and possibly reactive species present in the gas attributable to exothermic reaction chemistry is the detonation/deflagration precursor referred to in the title of this invention.

Temperature/pressure fluctuation measurements in gases much smaller than required for this invention are routinely utilized in photo thermal spectroscopes [e.g. photo acoustic, phase fluctuation, photothermal deflection spectroscopies; for specific example see Fluckiger, Lin, Marlow (1985)] to measure trace quantities of specific materials. In those spectroscopies, the source of heat is the dissipation of energy absorbed by molecules due to laser irradiation at spectral absorption wavelengths uniquely characteristic of the specific molecules of interest. No chemical reactions are involved in photothermal spectroscopies. In detonation/deflagration precursor detection, the subject of this invention, the source of heat is the exothermic chemical reactions which cause detonations and deflagrations and whose molar energy release is orders of magnitude greater than the thermal energies involved in the excitation-deexcitation-thermal-dissipation cycle of the molecules detected in photothermal spectroscopies. The most typical example of this exothermic reaction chemistry is oxidation of the "fuel" species by the oxygen in the air. Thus, the reaction of oxygen with the fuel species is the amplifier whose thermal output is utilized to indicate the presence of the hazardous materials. Alternatively, a specific oxidizable or reducible gas or aerosol if matched with a reducible or oxidizable reactive partner will also react exothermically and the thermal output can be used similarly as described for conventional oxidation. This exothermic chemistry causes perturbations in temperature and/or pressure and possibly other properties of the gas which can be detected in different ways including but not limited to the following: (1) by their effects upon the path of a beam of light or upon the paths of an array of beams of light used to passively probe the gas; (2) by the temperature profile of the gas as detected by an array of thermocouples or thermistors; (3) by the detection of electrical charges liberated by the exothermic reaction chemistry which can be monitored by ion probes or electrical conductivity setups; (4) by measurement of the pressure pulse accompanying the temperature gradient; (5) by measurement of scintillation luminescence (i.e. prompt and/or delayed fluorescence and phosphorescence) due to exothermic reactions using photodetectors For optical deflection detection, the essential element of this method is that the index of refraction of a gas is extremely sensitive to its temperature and pressure and a gradient in the index of refraction causes a deflection in the path of a beam of light. Unlike photothermal spectroscopies which generate very small temperature changes, the temperature-pressure pulse as generated in the device described above is large. Because of its magnitude and the short time scale of the energy deposition by the spark discharge, a sharp, transient gradient in the index of refraction of the air (or background gas) occurs which in turn leads to a substantial deflection of the light from its unperturbed path. Consequently, temperature/pressure perturbations due to exothermic chemistry (i.e. combustion as opposed to spectral absorption and dissipation in photothermal spectroscopy) as described here are readily detectable by their effects upon light passing through the gas and do not require the same degree of stabilization and sensitivity typically required in photothermal spectroscopic measurements.

Temperature/pressure transients that differ from those occurring in a gas devoid of exothermically reacting species indicate the occurrence of exothermic reaction chemistry in the gas in question. Since this is the chemistry which is responsible for detonations and deflagrations, these anomalous perturbations, or "precursors", identify the presence of gas, vapor, and/or aerosols that participate in exothermic reaction chemistry and quantification of the precursors can be made to identify when the gas is approaching a hazardous condition. Since any material in the gas phase that undergoes exothermic reaction chemistry in response to an initiator may also be quantified by this family of methods herein entitled "detonation/deflagration precursor detection", these methods may also be utilized for other purposes unrelated to detonation/deflagration prevention.

While this invention and the illustrative example cited herein have been formulated for transient precursor detection, nothing herein shall be construed as limiting the interpretation and utilization of these principles solely to transient cases. For example, a continuously-acting initiator in a flowing gas stream will provide a plume of elevated temperature that will dissipate with distance downstream from the initiator. If exothermically reactive species are present in the gas phase, then the initiator will force their reaction which will be accompanied by the generation of excess heat. This additional energy will be manifested downstream of the initiator by an extended distance for thermal decay of the plume as well as other characteristics of the plume that differ from the characteristics of the plume in the absence of exothermic reactions.

What is claimed is:

1. An apparatus for detecting a detonation-deflagration potential of a gas-borne material, comprising:

a chamber arranged to receive a sample of the gas-borne material, the gas-borne material having a concentration below a minimum explosive concentration;

an initiator which initiates an exothermic reaction of the gas-borne material within a localized initiation zone in the chamber, wherein the exothermic reaction generates a detonation-deflagration precursor in background gas outside the initiation zone;

a detector disposed outside the initiation zone and arranged to detect perturbations in the background gas; and a discriminator coupled to the detector to identify perturbations which are precursors.

2. The apparatus of claim 1, wherein the initiator is radiant energy.

3. The apparatus of claim 1, wherein the initiator is changing thermodynamic variable of the sample.

4. The apparatus of claim 1, wherein the initiator is a spark discharge.

5. The apparatus of claim 1, wherein the initiator is microwave energy.

6. The apparatus of claim 1, wherein the initiator is a hot wire.

7. The apparatus of claim 1, wherein the initiator is infrared energy.

8. The apparatus of claim 1, wherein the initiator is a laser.

9. The apparatus of claim 1, wherein the detector is a light detector which detects perturbations in the path of light.

10. The apparatus of claim 1, wherein the detector is a sensor which measures at least one characteristic from a group consisting of electrical charge, conductivity, and resistivity.

11. The apparatus of claim 1, wherein the detector is a pressure transducer.

12. The apparatus of claim 1, wherein the discriminator comprises a means for measuring at least one characteristic of the perturbations detected relative to at least one characteristic of background gas devoid exothermically reactive materials.

13. The apparatus of claim 1, further comprising a plurality of detectors disposed outside the initiation zone at spaced apart locations relative to the initiator, the detectors coupled to the discriminator and arranged to detect perturbations in the background gas.

14. An apparatus for detecting a detonation-deflagration potential of a gas-borne material, comprising:

a chamber arranged to receive a sample of the gas-borne material, the gas-borne material having a concentration below a minimum explosive concentration;

a spark discharge which initiates an exothermic reaction of the gas-borne material within a localized initiation zone in the chamber, wherein the exothermic reaction generates a transient gradient in an index of refraction of background gas outside the initiation zone;

a laser having a beam with an unperturbed path traversing the chamber outside of the initiation zone, the transient gradient in the index of refraction causing a deflection of the beam from the unperturbed path;

a detector arranged to measure the deflection of the beam from the unperturbed path; and a discriminator coupled to the detector to identify beam deflections which indicate a detonation-deflagration precursor.

15. An apparatus for detecting a detonation-deflagration potential of a gas-borne material, comprising:

a chamber arranged to receive a sample of the gas-borne material, the gas-borne material having a concentration below a minimum explosive concentration;

an initiator which initiates an exothermic reaction of the gas-borne material within a localized initiation zone in the chamber, wherein the exothermic reaction generates a detonation-deflagration precursor in background gas outside the initiation zone; and a detector disposed outside the initiation zone and arranged to detect perturbations in the background gas, the detector located a sufficient distance from the initiator and arranged such that only perturbations resulting from exothermie reaction chemistry are detected.

* * * * *

UNITED STATES PATENT AND TRADEMARK OFFICE
CERTIFICATE OF CORRECTION

PATENT NO. : 6,001,308
DATED : December 14, 1999
INVENTOR(S) : William H. MARLOW et al.

It is certified that error appears in the above-identified patent and that said Letters Patent is hereby corrected as shown below:

On Column 4, lines 27-28, after "detonation/deflagration" delete "nation/deflagration".

On Column 5, line 21, after "of this patent" delete "dr".

Signed and Sealed this

Eighth Day of August, 2000

Attest:

Q. TODD DICKINSON

*Attesting Officer*   *Director of Patents and Trademarks*